United States Patent [19]

Lubowitz et al.

[11] Patent Number: 4,547,553
[45] Date of Patent: Oct. 15, 1985

[54] POLYBUTADIENE MODIFIED POLYESTER COMPOSITIONS

[75] Inventors: Hyman R. Lubowitz, Rolling Hills Estates, Calif.; Clyde H. Sheppard, Bellevue, Wash.

[73] Assignee: The Boeing Company, Seattle, Wash.

[21] Appl. No.: 725,515

[22] Filed: Apr. 22, 1985

Related U.S. Application Data

[63] Continuation of Ser. No. 402,932, Jul. 29, 1982, abandoned.

[51] Int. Cl.$^4$ .............................................. C08G 63/54
[52] U.S. Cl. .................................... 525/384; 525/385; 525/386; 528/125; 528/126; 528/128; 528/173; 528/192; 528/193; 528/194; 528/195; 528/205
[58] Field of Search .................... 525/384, 385, 386; 528/125, 126, 128, 173, 192, 193, 194, 195, 205

[56] References Cited

U.S. PATENT DOCUMENTS

| | | |
|---|---|---|
| Re. 29,316 | 7/1977 | Bargain et al. ................... 528/353 |
| 3,236,808 | 2/1966 | Goldberg et al. . |
| 3,262,914 | 7/1966 | Goldberg et al. . |
| 3,265,708 | 8/1966 | Stiteler ............................ 260/326.5 |
| 3,355,272 | 11/1967 | D'Alessandro . |
| 3,453,236 | 7/1969 | Culbertson . |
| 3,454,673 | 7/1969 | Schmidt et al. ................... 525/445 |
| 3,530,087 | 9/1970 | Hays et al. . |
| 3,536,670 | 10/1970 | Aelony et al. ....................... 528/170 |
| 3,562,223 | 2/1971 | Bargain et al. . |
| 3,563,951 | 2/1971 | Radlmann et al. ................ 528/951 |
| 3,631,222 | 12/1971 | Vogel et al. . |
| 3,641,207 | 2/1972 | Lauchlan . |
| 3,652,710 | 3/1972 | Holub et al. . |
| 3,658,938 | 4/1972 | Kwiatkowski et al. . |
| 3,663,507 | 3/1972 | Vogel et al. . |
| 3,699,075 | 10/1972 | Lubowitz et al. ................... 528/172 |
| 3,708,439 | 1/1973 | Sayigh et al. . |
| 3,729,446 | 4/1973 | Holub et al. ...................... 526/262 |
| 3,761,441 | 9/1973 | D'Alessandro et al. ............ 524/600 |
| 3,763,101 | 10/1973 | Jones et al. . |
| 3,770,697 | 11/1973 | Holub et al. ...................... 528/196 |
| 3,773,718 | 11/1973 | Klebe et al. . |
| 3,787,363 | 1/1974 | Staniland et al. . |
| 3,803,081 | 4/1974 | Lubowitz et al. ................... 528/196 |
| 3,812,159 | 5/1974 | Lubowitz ........................ 260/346.3 |
| 3,839,287 | 10/1974 | Kwiatkowski et al. . |
| 3,879,349 | 4/1975 | Bilow et al. . |
| 3,897,393 | 7/1975 | Lu . |
| 3,897,395 | 7/1975 | D'Alelio . |

(List continued on next page.)

FOREIGN PATENT DOCUMENTS

| | | |
|---|---|---|
| 71068 | 7/1981 | Japan . |
| 2002378 | 5/1978 | United Kingdom . |

OTHER PUBLICATIONS

Sheppard, C. H. and House, E. E., "Development of Modified Polysulfone Resins", Final Report on Contract N00019-80-C-0609, Boeing Aerospace Co., Seattle, Wash., 98124, Dec. 1981.

Sheppard, C. H., House, E. E. and Stander, M., "Advanced Thermoplastic Composite Development", Reinforced Plastics Composites Institute, Society of the Plastic Industry Inc., Feb. 16-20, 1981.

"Graphite Reinforced Thermoplastic Composites," Jaquish et al. Navy Report D180-26067-1 prepared for Naval Air Systems Command.

U.S. Department of the Navy under Contract N00019-79-C-0203, (Aug. 1980) (*Navy Report*).

*Primary Examiner*—Lester L. Lee
*Attorney, Agent, or Firm*—40Finnegan, Henderson, Farabow, Garrett & Dunner

[57] ABSTRACT

Oligomers formed by reacting polybutadiene and phenoxyphenyl components are cross-linked to form resins which are thermoplastic in nature, resist attack by organic solvents, and are shapable at temperatures of about 400° F. The oligomers may be used to impregnate materials, such as fabrics, to form resin composites which are also thermoplastic and solvent resistant upon cross-linking.

21 Claims, 1 Drawing Figure

U.S. PATENT DOCUMENTS

| | | | |
|---|---|---|---|
| 3,920,768 | 11/1975 | Kwiatkowski . | |
| 3,935,167 | 1/1976 | Marvel et al. . | |
| 3,956,320 | 5/1976 | Heath et al. | 562/468 |
| 3,972,902 | 8/1976 | Heath et al. | 549/241 |
| 3,975,862 | 8/1976 | Doan | 49/409 |
| 3,998,786 | 12/1976 | D'Alelio et al. | 528/353 |
| 4,005,134 | 1/1977 | Markezich | 260/343.4 |
| 4,020,069 | 4/1977 | Johnson et al. | 528/170 |
| 4,058,505 | 11/1977 | D'Alelio | 528/353 |
| 4,064,289 | 12/1977 | Yokoyama et al. | 427/82 |
| 4,100,137 | 7/1978 | Lemieux et al. | 525/385 |
| 4,128,574 | 12/1978 | Markezich et al. | 562/473 |
| 4,175,175 | 11/1979 | Johnson et al. | 528/125 |
| 4,176,223 | 11/1979 | Irwin | 528/170 |
| 4,239,883 | 12/1980 | Stenzenberger | 528/322 |
| 4,288,607 | 9/1981 | Bier | 528/192 |
| 4,297,474 | 10/1981 | Williams, III et al. | 528/170 |
| 4,414,269 | 11/1983 | Lubowitz et al. | 428/290 |
| 4,476,184 | 10/1984 | Lubowitz et al. | 428/288 |

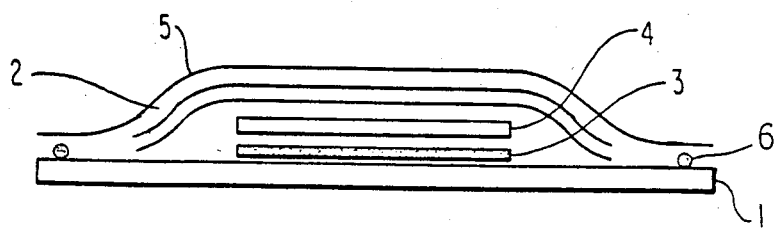

POLYBUTADIENE MODIFIED POLYESTER COMPOSITIONS

The Government has rights in this invention pursuant to Contract No. N00019-80-C-0609 awarded by the United States Navy.

This application is a continuation of application Ser. No. 402,932 filed July 29, 1982, now abandoned.

BACKGROUND OF THE INVENTION

The present invention relates to resins containing polymer chains that bear functional chemical groups and to the products thereof. In particular, the present invention relates to resins which are thermoplastic in nature.

For many applications, it is desirable to employ thermoplastic resins. Although such resins and their application areas are well-known, the use of thermoplastic resin reinforced by fiber is a relatively new art. The advantages of this art, however, are significant. Fiber toughens and stiffens the resin to produce high-performance products. At the same time, processing is facilitated because the fiber-reinforced resin maintains its thermoplastic character. For example, a sheet of fiber-reinforced resin can be heated and then stamped into desired shapes with approriate metal dies. Furthermore, shapes can be altered when desired.

On the other hand, although thermosetting resins are generally used in fabricating fiber-reinforced composites, fashioning shapes by thermoforming is not readily possible when thermosetting resins are used. Such products must be fashioned within the constraints of dies. Once formed, they cannot be reshaped; thus, errors are not correctable and shape adjustments are not possible. A sheet of fiber-reinforced thermosetting resin, fully cured, cannot be thermoformed into desired shapes.

Although thermoplastic resins exhibit processing advantages over thermosetting resins, they exhibit, in general, a serious deficiency in properties, i.e., the tendency to be solvated and thus weakened by organic solvents. This deficiency has severely limited application of fiber-reinforced thermoplastic resin composites. For example, in the preparation of circuit boards, boards prepared from fiber-reinforced thermoplastic resin composites cannot be cleaned by solvents commonly used in he manufacture of circuit boards. Also, in the use of thermoplastic components for aircraft, a significant amount of product loss is incurred when aircraft hydraulic fluids and cleaning fluids come into contact with the composites.

SUMMARY OF THE INVENTION

It is, therefore, a main object of the present invention to provide oligomers from which thermoplastic resins in general and fiber-reinforced thermoplastic resin composites in particular which overcome the above-mentioned drawbacks can be produced.

It is a more specific object of the present invention to provide oligomers from which thermoplastic resins in general and fiber-reinforced thermoplastic resin composites in particular which are resistant to attack by organic solvents can be produced.

Another object of the present invention is to provide oligomers from which thermoplastic, solvent resistant resins in general and fiber-reinforced thermoplastic, solvent resistant resin composites in particular which can be shaped or reshaped at a temperature of about 400° F. in a relatively short period of time can be produced.

An additional object of the present invention is to provide oligomers from which thermoplastic resins in general and fiber-reinforced thermoplastic resin composites in particular which possess excellent adhesive properties can be produced.

a still additional object of the present invention is to provide oligomers from which fiber-reinforced thermoplastic resin composites useful as repair materials for composite structures in general, and aircraft and spacecraft in particular, can be produced.

A further object of the present invention is to provide oligomers from which fiber-reinforced thermoplastic resin composites that are dimensonally rigid and yet highly resistant to mechanical impact and thermal shock can be produced.

a still further object of the present invention is to provide oligomers from which fiber-reinforced thermoplastic resin composites that are resistant to embrittlement at low temperatures can be produced.

Additional objects and advantages of the invention will be set forth in part in the description which follows, and in part will be obvious from the description, or may be learned by practice of the invention. The objects and advantages of the invention may be realized and attained by means of instrumentalities and combinations particularly pointed out in the appended claims.

To achieve the objects, and in accordance with the purpose of the invention, as embodied and broadly described herein, the invention comprises an oligomer formed by reacting: a polybutadiene component selected from the group consisting of hydroxy terminated polybutadiene, carboxy terminated polybutadiene, and mixtures thereof, and a phenoxyphenyl component having the formula

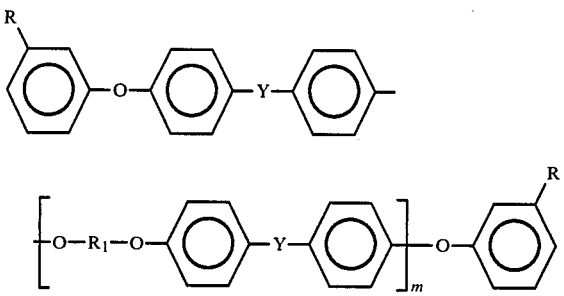

wherein Y is selected from the group consisting of sulfone, sulfoxide, sulfide, carbonyl, and perfluoroisopropanyl, R is selected from the group consisting of acid chloride, carboxy, hydroxy and lower aliphatic ester, $R_1$ is selected from the group consisting of diphenyleneisopropane, phenylene, biphenylene, diphenylenesulfide, diphenylenesulfone, diphenylene ether, and diphenylenehexafluoropropane, and m is an integer of from 0 to 4, and wherein the molar ratio of the components is selected such that the hydroxy groups of the polybutadiene component and the acid chloride, carboxy and lower aliphatic ester groups of the phenoxyphenyl component are reacted at equivalents or thereabouts, and the carboxy groups of the polybutadiene component and the hydroxy groups of the phenoxyphenyl component are reacted at equivalents or thereabouts; and wherein the polybutadiene component constitutes from about 1 to about 25% by weight of the oligomer and the molecular weight of the oligomer is between about 5,000 and about 40,000.

To further achieve the objects of the present invention, the invention comprises an oligomer formed by reacting the aforementioned polybutadiene and phenoxyphenyl components with a difunctional component selected from the group consisting of dialcohol, dicarboxylic acid, diacid chloride and mixtures thereof; the molar ratio of the components being such that the hydroxy groups of the difunctinal and polybutadiene components are reacted at equivalents or thereabouts with the acid chloride, carboxy and lower aliphatic ester groups of the phenoxyphenyl component, and the carboxy and acid chloride groups of the difunctional and polybutadiene components are reacted at equivalents or thereabouts with the hydroxy groups of the phenoxyphenyl component; and wherein the polybutadiene component constitutes from about 1 to about 25% by weight of the oligomer, and the phenoxyphenyl component constitutes from about 40 to about 95% by weight of the oligomer, and wherein the molecular weight of the oligomer is between about 5,000 and about 40,000.

To further achieve the objects of the present invention, the invention comprises an oligomer useful for forming a solvent resistant, thermoplastic resin or resin composite comprising: polybutadiene units selected from the group consisting of oxygen terminated polybutadiene units, carbonyl terminated polybutadiene units, and mixtures thereof; and phenoxyphenyl units having the formula

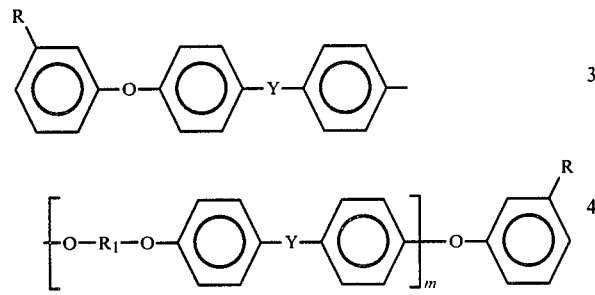

wherein y is selected from the group consisting of sulfone, sulfoxide, sulfide, carbonyl, and perfluroisopropanyl, R is selected from the group consisting of oxygen and carbonyl, $R_1$ is selected from the group consisting of diphenyleneisopropane, phenylene, biphenylene, diphenylenesulfide, diphenylenesulfone, diphenylene ether, and diphenylenehexafluoropropane, and m is an integer of from 0 to 4; and wherein the polybutadiene units constitute from about 1 to about 25% by weight of the oligomer, and the oligomer has a molecular weight of between about 5,000 and about 40,000.

To further achieve the objects of the present invention, the invention comprises a solvent resistant, thermoplastic resin formed by cross-linking any of the aforementioned oligomers.

To further achieve the objects of the present invention, the invention comprises a solvent resistant, thermoplastic, fiber-reinforced, resin composite formed by impregnating a fabric with any of the aforementioned oligomers and cross-linking the oligomers.

To further achieve the objects of the present invention, the invention comprises the method comprising the step of using the aforementioned oligomers, resins and resin composites as adhesives.

To further achieve the objects of the present invention the invention comprises the method comprising the step of using the aforementioned resin composites as a repair material.

The foregoing and other objects, features, and advantages of the present invention will be made more apparent from the following description of the preferred embodiment. The accompanying drawings which are incorporated in and constitute a part of this specification, illustrate an embodiment of the invention and together with the description serve to explain the principles of the invention.

BRIEF DESCRIPTION OF THE DRAWING

The drawing illustrates the curing of fabric impregnated with the polymer of the present invention in a vacuum bag.

DESCRIPTION OF THE PREFERRED EMBODIMENTS

Reference will now be made in detail to the present preferred embodiments of the invention.

In accordance with the invention, as embodied herein, the oligomers of the present invention are formed by reacting: a polybutadiene component selected from the group consisting of hydroxy terminated polybutadiene, carboxy terminated polybutadiene, and mixtures thereof, and a phenoxyphenyl component having the formula

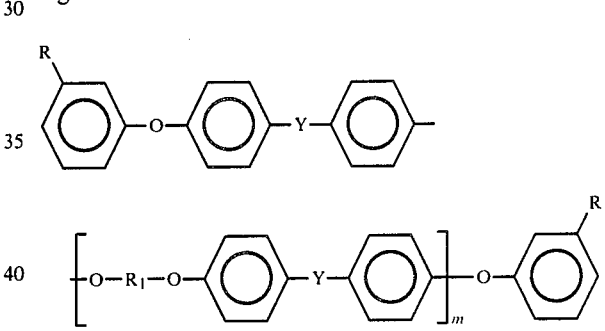

wherein Y is selected from the group sulfone, sulfoxide, sulfide, carbonyl, and perfluoroisopropanyl, R is selected from the group acid chloride, carboxy, hydroxy and lower aliphatic ester, $R_1$ is selected from the group consisting of diphenyleneisopropane, phenylene, biphenylene, diphenylenesulfide, diphenylenesulfone, diphenylene ether, and diphenylenehexafluoropropane and m is an integer having a value of from 0 to 4. Preferably, a third reactant, a difunctional component selected from the group consisting of dialcohol, dicarboxylic acid, diacid chloride and mixtures thereof is also employed.

The hydroxy, carboxy, acid chloride, and lower aliphatic ester groups of the various components are reactive and make the reaction possible. In the two component system, the molar ratio of the polybutadiene and phenoxyphenyl components is selected such that the hydroxy groups of the polybutadiene component and the acid chloride, carboxy and lower aliphatic ester groups of the phenoxyphenyl component are reacted at equivalents or thereabouts, and the carboxy groups of the polybutadiene component and the hydroxy groups of the phenoxyphenyl component are reacted at equivalents or thereabouts. Similarly, in the three component system, the molar ratio of the polybutadiene, phenoxyphenyl and difunctional components is selected such that the hydroxy groups of the polybutadiene and difunctional components are reacted at equivalents or therabouts with the acid chloride, carboxy, and lower aliphatic ester groups of the phenoxyphenyl component and the carboxy and acid chloride groups of the polybutadiene and difunctional components are reacted at equivalents or thereabouts with the hydroxy groups of the phenoxyphenyl component.

The molecular weight of the oligomer may be between about 5,000 and about 40,000, but it is preferably between about 10,000 and about 30,000, and still more preferably between about 15,000 and about 25,000. Mixtures of oligomers having molecular weights within these ranges may also be used, for example, a mixture of an oligomer having a molecular weight of 10,000 with one having a molecular weight of 30,000, or a mixture of an oligomer with a molecular weight of 15,000 with one having a molecular weight of 20,000 or 25,000. Within these ranges, the oligomers can be cross-linked to form resins that are insoluble while retaining thermoplasticity. The oligomer itself, however is soluble and therefore may be easily processed such as by impregnating a fabric or glass or other appropriate material.

An oligomer with a molecular weight lower than about 5,000 may upon cross-linking form a resin having insufficient sized links between cross-linkings such that the resin would lose its thermoplastic properties, and consequently, suffer the disadvantages of thermosetting resins. On the other hand, if the oligomer has a molecular weight of more than about 40,000, upon cross-linking the size of the links between cross-linkings may be too large and the resulting resin will have inadequate solvent resistance, as with prior thermoplastic resins. Within the ranges described above, the cross-linked oligomers have the beneficial properties of both thermoplastic and thermosetting resins without the disadvantages of either.

The polybutadiene component used in the present invention may be either a hydroxy terminated polybutadiene, a carboxy terminated polybutadiene, or mixtures thereof. (Of course, whenever a carboxy terminated polybutadiene is used, there must be an equivalent amount of a dihydroxy phenoxyphenyl component for the carboxy terminated polybutadiene to react with.) Preferably the polybutadiene has a predominantly atactic and vinyl composition. It is also desirable that the polybutadiene be more than 60% 1,2 configuration with the remainder being 1,4 configuration. More preferably, the polybutadiene composition is more than 90% 1,2 configuration, with the remainder being 1,4 configuration.

The polybutadiene component must constitute from about 1 to about 25% by weight of the oligomer. Preferably, the polybutadiene component constitutes from about 3 to about 20% by weight of the oligomer. More preferably, the polybutadiene component constitutes from about 5 to about 10% by weight of the oligomer. An oligomer with a polybutadiene content higher than about 25% by weight would undergo excessive cross-linking and lose its thermoplastic properties, and, consequently, suffer the disadvantages of thermosetting resins. If the oligomer has a polybutadiene content less than about a 1% by weight, insufficient cross-linking will occur and the resulting resin will have inadequate solvent resistance, as with prior thermoplastic resins. Within the ranges described above, however, the cross-linked oligomer has the beneficial properties of both thermoplastic and thermosetting resins without the disadvantages of either.

The phenoxyphenyl component of the present invention has the following structure:

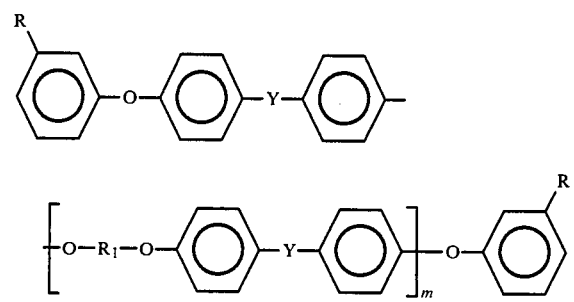

wherein Y is selected from the group sulfone

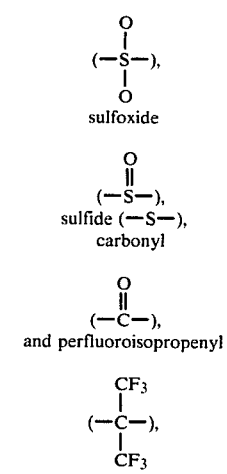

sulfoxide sulfide (—S—), carbonyl and perfluoroisopropenyl

R is selected from the group acid chloride

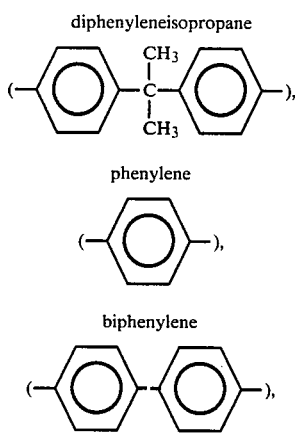

carboxy (—COOH), hydroxy (—OH) and lower aliphatic ester (—COOX where X is an alkyl group having from 1 to 5 carbon atoms), $R_1$ is selected from the group diphenyleneisopropane phenylene biphenylene -continued diphenylenesulfide

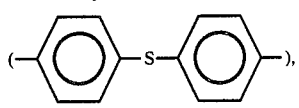

diphenylenesulfone

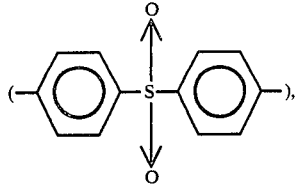

diphenylene ether

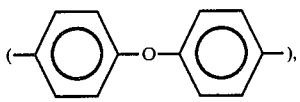

and diphenylenehexafluoropropane

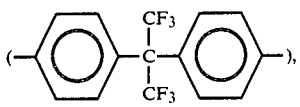

and m is an integer having a value of from 0 to 4. Preferably Y is a sulfone, R is an acid chloride in the para or meta position, and m is 0. When m is other than 0, $R_1$ is preferably diphenyleneisopropane. Good results have been achieved where the phenoxyphenyl component is the acid chloride of bis(4-carboxyphenoxyphenyl) sulfone.

The phenoxyphenyl component must constitute at least about 40% by weight of the oligomer, preferably between about 40 and about 95% by weight of the oligomer, more preferably between about 60 and about 90% by weight of the oligomer and most preferably between about 70 and about 80% by weight of the oligomer.

The difunctional component used in the present invention may be either a dialcohol, dicarboxylic acid, diacid chloride or mixtures thereof. Either aliphatic or aromatic dialcohols, dicarboxylic acids and diacid chlorides may be used.

Typical aliphatic dialcohols (glycols) that may be used in the process of the present invention include:

TABLE I

Aliphatic dialcohols (glycols)

HO—CH$_2$—CH$_2$—OH
(ethylene glycol)
HO—CH$_2$—CHOH—CH$_2$—CH$_3$
(1,2-butane diol)
HO—CH$_2$—CH$_2$—CHOH—CH$_3$
(1,3-butane diol)
HO—CH$_2$—CH$_2$—CH$_2$—CH$_2$—OH
(1,4-butane diol)
HO—CH$_2$—CH$_2$—CH$_2$—CH$_2$—CH$_2$—CH$_2$—OH
(1,6-hexane diol)

Typical aromatic dialcohols that may be used in the process of the present invention include:

TABLE II

Aromatic dialcohols

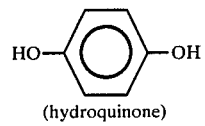

(hydroquinone)

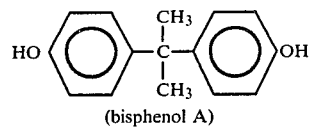

(bisphenol A)

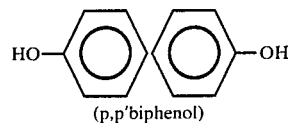

(p,p'biphenol)

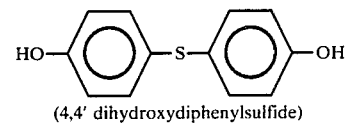

(4,4' dihydroxydiphenylsulfide)

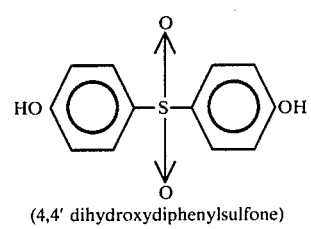

(4,4' dihydroxydiphenylsulfone)

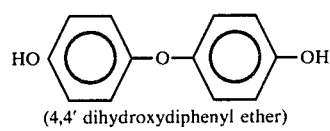

(4,4' dihydroxydiphenyl ether)

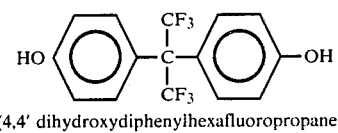

(4,4' dihydroxydiphenylhexafluoropropane)

Each of the illustrated aromatic dialcohols could also be replaced by the ortho or meta isomer. The compounds may be substituted on the aromatic rings with one or more halogens, lower alkyl groups or lower alkoxy groups (1 to 4 carbon atoms). A low cost aromatic dialcohol suitable for use in he present invention is bisphenol A. Replacing a portion of the bisphenol A with other dialchohols can contribute other valuable properties, for example, it is believed that use of 4,4' dihydroxydiphenylhexafluoropropane will enhance the flame resistance characteristics of the resulting product. Order of addition of reactants may be varied to yield either random or block oligomers.

For purposes of the present invention any of the above-listed aliphatic or aromatic dialcohols can be replaced with their counterpart dicarboxylic acids or diacid chlorides. Moreover, mixtures of the various dialcohols, dicarboxylic acids and diacid chlorides could also be used. Of course, whenever a dicarboxylic acid or a diacid chloride is used as the difunctional component, there must be an equivalent amount of a dihydroxy phenoxyphenyl component for the dicarboxylic acid to react with.

The oligomers of the present invention may be cross-linked to form solvent resistant, thermoplastic resins which can be shaped at temperatures of about 400° F. Cross-linking can be effected by activating the unsaturation in the polybutadiene component with an organic peroxide and then heating. Suitable organic peroxides include: LUPERSOL 101, and LUPERSOL 130. Alternatively, cross-linking can be effected by other common techniques known to the art such as ultraviolet radiation.

The oligomers of the present invention may be used to impregnate a fabric to form a prepreg. The prepreg may then be cured, such as by vacuum bagging and heating at an elevated temperature while under pressure. This is illustrated in the drawing, in which 1 is a caul (a metal backing for applying a surface finish), 2 is a vacuum source, 3 is the prepreg, 4 is a pressure plate, 5 is a nylon film, and 6 is Kisch (zinc chromate tape).

The oligomer of the present invention can be used to impregnate a fabric to form a prepreg either before or after it has been cross-linked. As embodied herein the preferred method of making a fiber reinforced resin composite from the oligomers of the present invention, comprises forming a solution of oligomer and organic peroxide in a suitable solvent, impregnating a fabric with this solution, and then curing/heating the impregnated fabric.

The thermoplastic resin of the present invention and the fiber-reinforced resin composite made therefrom are solvent resistant and thermoplastic in nature. Additionally, they can be shaped at temperatures of about 400° F. Furthermore, they have desirable adhesive properties, and thus can be used as adhesives. Moreover, the composites have desirable repair properties, and can be used as repair material for composite structures in general and aircraft and spacecraft in particular.

The following examples are presented to illustrate the various features of the invention.

EXAMPLE 1

(Preparation of Acid Chloride of Bis(4-Carboxyphenoxyphenyl) Sulfone)

The acid chloride of bis(4-carboxyphenoxyphenyl) sulfone was prepared as follows: The sulfone diacid bis(4-carboxyphenoxyphenyl) sulfone was added to thionyl chloride and the mixture was heated at 55° C. until the evolution of HCl and $SO_2$ gas ceased. Excess thionyl chloride was removed by distillation, and the product dissolved in warm benzene and recrystallized by adding cyclohexane. (Yields 80–85%; M.P. 173°–175° C.)

EXAMPLE 2

(Preparation of Oligomer With Acid Chloride of Bis(4-Carboxyphenoxyphenyl) Sulfone)

A solution of 10.64 grams of 1,6 hexane diol (0.9 Eq), 16.00 grams of hydroxy terminated 1,2 polybutadiene Eq Wt 790 (0.1 Eq), and 223.8 grams of pyridine were placed in a three neck round bottom flask. 50.89 grams of the acid chloride of bis(4-carboxyphenoxyphenyl) sulfone (1.0 Eq) prepared in Example 1 was added and the solution was refluxed for eight hours at 109°–113° C. The polyester sulfone crystallized in the pyridine and was recovered by filtration. The precipitate was then thoroughly washed in $H_2O$ until no residual chloride could be detected by adding $AgNO_3$ to the wash water. (Softening point—90° C. with medium viscosity at 55° C.). Residual chloride was determined on the polyester sulfone product to be less than 0.1%.

EXAMPLE 3

(Preparation and Testing of Fiber-Reinforced Resin Composite From Oligomer of Example 2)

The product of Example 2 in a solution of $MeCl_2$ and an organic peroxide, Lupersol 101 (5 pbw of peroxide to 100 pbw of the resin of Example 2) was prepreged onto 3K-70-PW T300 graphite fabric. The coated T300 graphite fabric was allowed to stand 72 hours at ambient conditions then cut and stacked into a ten ply laminate. The prepreg stack was then placed in a vacuum bag, cured for 2 hours at 177° C. under pressure (15 psia).

Solubility in Methylene Chloride

A sample of the composite was machined into a 1×0.5-inch coupon and placed in a bottle containing methylene chloride. The coupon was observed for ply separation. The result of this testing revealed conclusively that the graphite composite of the present invention remained intact, with only slight swelling after immersion times to 2 months. This test amply demonstrated that the cross-linked oligomers of the present invention form resins which are solvent resistant.

Mechanical Properties

The composites under consideration were machined into short beam shear specimens and tested at ambient conditions and 220° F. using the following procedure. The testing was accomplished on a flexure testing fixture using three-point loading with a span of four times the specimen thickness. Results of testing are reported below:

| Short Beam Shear, ksi | |
|---|---|
| Room Temperature | 220° F. |
| 2.2 | 1.4 |

EXAMPLE 4 (PROJECTED SYNTHESIS)

(Preparation of Thermoplastic Resin With Alternate Aliphatic Dialcohol)

Place in a three-neck round bottom flask a solution of 1,4 butane diol (0.95 Eq), hydroxy terminated 1,2 polybutadiene (Equivalent weight 790) (0.05 Eq) and pyridine. To this solution the acid chloride of bis(4-carboxyphenoxyphenyl) sulfone (1.0 Eq) is added and solution refluxed eight hours (109°–113° C.). The polyester sulfone is recovered by removing excess pyridine by vacuum distillation, placing the aremaining product in acetone, and precipitating by addition of petroleum ether.

EXAMPLE 5 (PROJECTED SYNTHESIS)

(Preparation of Thermoplastic Resin with Aromatic Dialcohol)

Place in a three-neck round bottom flask a solution of bisphenol A (0.95 Eq), hydroxy terminated 1,2 polybutadiene (0.05 Eq) and pyridine. To the solution add the acid chloride of bis(4-carboxyphenoxyphenyl) sulfone (1.0 Eq) and reflux eight hours at (109°–113° C.). The polyester sulfone is recovered by removing excess pyridine by vacuum distillation, filtering he precipitate and thoroughly washing until no residual chloride can be detected by adding AgNO₃.

EXAMPLE 6 (PROJECTED SYNTHESIS)

(Preparation of Oligomer with Aliphatic Dicarboxylic Acid)

The reaction product obtained by reacting adipic acid, carboxy terminated 1,2 polybutadiene, and bis(4-hydroxyphenoxyphenyl) sulfone.

EXAMPLE 7 (PROJECTED SYNTHESIS)

(Preparation of Oligomer with Aromatic Dicarboxylic Acid)

The reaction product obtained by reacting terephthalic acid, carboxy terminated 1,2 polybutadiene, and bis(4-hydroxyphenoxyphenyl) sulfone.

EXAMPLE 8 (PROJECTED SYNTHESIS)

(Preparation of Oligomer with Carboxy Terminated Polybutadiene)

The reaction product of carboxy terminated 1,2 polybutadiene, suberic acid, and bis(4-hydroxyphenoxyphenyl) sulfone.

EXAMPLE 9 (PROJECTED SYNTHESIS)

(Preparation of Oligomer with Phenoxyphenyl Dicarboxylic Acid)

The reaction product of bis(3-carboxyphenoxyphenyl) sulfone, 1,6 hexane diol and hydroxy terminated 1,2 polybutadiene.

EXAMPLE 10 (PROJECTED SYNTHESIS)

(Preparation of Oligomer with Phenoxyphenyl Dialiphatic Ester)

The reaction product of bis(4-methylcarboxylatephenoxyphenyl sulfone, 1,4 butane diol, and hydroxy terminated 1,2 polybutadiene.

EXAMPLE 11 (PROJECTED SYNTHESIS)

(Preparation of Oligomer with Phenoxyphenyl Dialcohol)

The reaction product of bis(4-hydroxyphenoxyphenyl) sulfone, isophthalic acid, and carboxy terminated 1,2 polybutadiene.

EXAMPLE 12 (PROJECTED SYNTHESIS)

(Preparation of Oligomer with Phenoxyphenyl Sulfoxide)

The reaction product of the acid cholride of bis(4-carboxyphenoxyphenyl) sulfoxide, ethylene glycol, and hydroxy terminated 1,2 polybutadiene.

EXAMPLE 13 (PROJECTED SYNTHESIS)

(Preparation of Oligomer with Phenoxyphenyl Sulfide)

The reaction product of the acid chloride of bis(4-carboxyphenoxyphenyl) sulfide, 1,3 butane diol, and hydroxy terminated 1,2 polybutadiene.

EXAMPLE 14 (PROJECTED SYNTHESIS)

(Preparation of Oligomer with Phenoxyphenyl Perfluoroisopropanyl)

The reaction product of the acid chloride of bis(4-carboxyphenoxyphenyl) perfluroisopropane, 4,4' dihydroxydiphenylsulfone, and hydroxy terminated 1,2 polybutadiene.

EXAMPLE 15 (PROJECTED SYNTHESIS)

(Preparation of Oligomer with Penoxyphenyl Carbonyl)

The reaction product of the acid chloride of bis (4-carboxyphenoxyphenyl) ketone, bisphenol A, and hydroxy terminated 1,2 polybutadiene.

It will be apparent to those skilled in the art that various modifications and variations can be made in the present invention without departing from the scope or spirit of the invention. Thus, it is intended that the present invention cover the modifications and variations of this invention provided that they come within the scope of the appended claims and their equivalents.

What is claimed is:

1. An oligomer formed by reacting: a polybutadiene component selected from the group consisting of hydroxy terminated polybutadiene, carboxy terminated polybutadiene, and mixtures thereof; and a phenoxyphenyl component having the formula

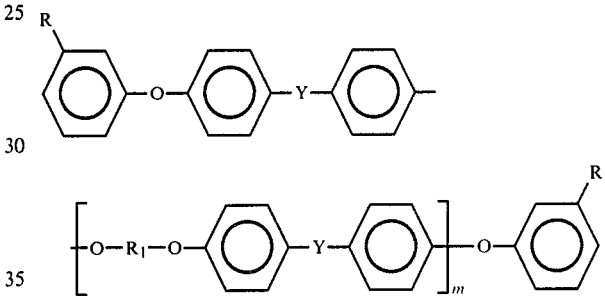

wherein Y is selected from the group consisting of sulfone, sulfoxide, sulfide, carbonyl, and perfluoroisopropanyl, R is selected from the group consisting of acid chloride, carboxy, hydroxy and lower aliphatic ester, $R_1$ is selected from the group consisting of diphenyleneisopropane, phenylene, biphenylene, diphenylenesulfide, diphenylenesulfone, diphenylene ether, and diphenylenehexafluoropropane, and m is an integer of from 0 to 4; and wherein the molar ratio of said components is selected such that the hydroxy groups of said polybutadiene component and the acid chloride, carboxy and lower aliphatic ester groups of said phenoxyphenyl component are reacted at equivalents or thereabouts, and the carboxy groups of said polybutadiene component and the hydroxy groups of said phenoxyphenyl component are reacted at equivalents or thereabouts; and wherein said polybutadiene component constitutes from about 1 to about 25% by weight of the oligomer; and the molecular weight of the oligomer is between about 5,000 and about 40,000.

2. An oligomer formed by reacting the polybutadiene and phenoxyphenyl cmponents of claim 1 with a difunctional component selected from the group consisting of dialcohol, dicarboxylic acid, diacid chloride and mixtures thereof; the molar ratio of said components being such that the hydroxy groups of said difunctional and polybutadiene components are reacted at equivalents or thereabouts with the acid chloride, carboxy, and lower aliphatic ester groups of said phenoxyphenyl component, and the carboxy and diacid chloride groups of said difunctional and polybutadiene components are reacted at equivalents or thereabouts with the hydroxy groups of said phenoxyphenyl component; and wherein said polybutadiene component constitutes from about 1 to about 25% by weight of the oligomer and said phenoxyphenyl component constitutes from about 40% to about 95% by weight of the oligomer; and wherein the molecular weight of said oligomer is between 5,000 and about 40,000.

3. The oligomer of claim 1 or 2 wherein said polybutadiene component constitutes from about 3 to about 20% by weight of the oligomer.

4. The oligomer of claim 3 wherein said polybutadiene component constitutes from about 5 to about 10% by weight of the oligomer.

5. The oligomer of claim 2 wherein said phenoxyphenyl component constitutes from about 60 to about 90% by weight of the oligomer.

6. The oligomer of claim 5 wherein said phenoxyphenyl component constitutes from about 70 to about 80% by weight of the oligomer.

7. The oligomer of claim 1 or 2 wherein Y is a sulfone and R is an acid chloride in the para or meta position.

8. The oligomer of claim 2 wherein said difunctional component is a dialcohol.

9. The oligomer of claim 8 wherein said dialcohol is selected from the group consisting of ethylene glycol, 1,2 butane diol, 1,3 butane diol, 1,4 butane diol, 1,6 hexane diol, hydroquinone, bisphenol A, p,p' biphenol, 4,4' dihydroxydiphenylsulfide, 4,4' dihydroxydiphenylsulfone, 4,4' dihydroxydiphenyl ether, 4,4' dihydroxydiphenylhexafluoropropane, and mixtures thereof.

10. The oligomer of claim 1 or 2 wherein said polybutadiene has a predominantly atactic and vinyl composition.

11. The oligomer of claim 1 or 2 wherein said polybutadiene composition is more than 60% 1,2 configuration, the remainder being 1,4 configuration.

12. The oligomer of claim 11 wherein said polybutadiene composition is more than 90% 1,2 configuration, the remainder being 1,4 configuration.

13. The oligomer of claim 1 or 2 wherein the molecular weight of the oligomer is between about 10,000 and about 30,000.

14. The oligomer of claim 13 wherein the molecular weight of the oligomer is between about 15,000 and about 25,000.

15. The oligomer of claim 2 wherein said polybutadiene component is a hydroxy terminated polybutadiene, said phenoxyphenyl component is a diacid chloride phenoxyphenyl sulfone and said difunctional component is a dialcohol.

16. The oligomer of claim 15 wherein said polybutadiene component is hydroxy terminated 1,2 polybutadiene, said phenoxyphenyl component is the acid chloride of bis(4-carboxyphenoxyphenyl) sulfone and said dialcohol is 1,6 hexane diol.

17. The oligomer of claim 15 wherein said polybutadiene component is hydroxy terminated 1,2 polybutadiene, said phenoxyphenyl component is the acid chloride of bis(4-carboxyphenoxyphenyl) sulfone and said dialcohol is 1,4 butane diol.

18. The oligomer of claim 15 wherein said polybutadiene component is hydroxy terminated 1,2 polybutadiene, said phenoxyphenyl component is the acid chloride of bis(4-carboxyphenoxyphenyl) sulfone and said dialcohol is bisphenol A.

19. An oligomer useful for forming a solvent resistant, thermoplastic resin or resin composite comprising: polybutadiene units selected from the group consisting of oxygen terminated polybutadiene units, carbonyl terminated polybutadiene units, and mixtures thereof; and phenoxyphenyl units having the formula

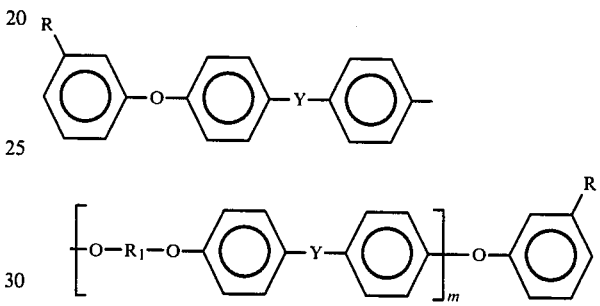

wherein y is selected from the group consisting of sulfone, sulfoxide, sulfide, carbonyl, and perfluroisopropanyl, R is selected from the group consisting of oxygen and carbonyl, $R_1$ is selected from the group consisting of diphenyleneisopropane, phenylene, biphenylene, diphenylenesulfide, diphenylenesulfone, diphenylene ether, and diphenylenehexafluoropropane, and m is an integer of from 0 to 4; and wherein said polybutadiene units constitute from about 1 to about 25% by weight of said oligomer, and said oligomer has a molecular weight of between about 5,000 and about 40,000.

20. The oligomer of claim 19 wherein Y is a sulfone, and R is a carbonyl in the para position.

21. The oligomer of claim 19 or 20 which further comprises: at least one unit selected from the group consisting of 1,6 oxygen terminated hexane, 1,6 carbonyl terminated hexane, 1,4 oxygen terminated butane, 1,4 carbonyl terminated butane, 1,2 oxygen terminated ethane, 1,2 carbonyl terminated ethane, 1,4oxygen terminated diphenyleneisopropane, 1,4 carbonyl terminated diphenyleneisopropane and wherein said phenoxyphenyl units constitute from about 40 to about 95% by weight of said oligomer.

* * * * *

UNITED STATES PATENT AND TRADEMARK OFFICE
CERTIFICATE OF CORRECTION

PATENT NO. : 4,547,553
DATED : October 15, 1985
INVENTOR(S) : Hyman R. Lubowitz et al.

It is certified that error appears in the above-identified patent and that said Letters Patent is hereby corrected as shown below:

Column 12, claim 2, line 2, "cmponents" should be --components--.

Column 14, claim 21, line 6, after "1,4" insert a space before "oxygen".

Signed and Sealed this

Eighteenth Day of March 1986

[SEAL]

Attest:

DONALD J. QUIGG

Attesting Officer

Commissioner of Patents and Trademarks